US012623987B2

(12) United States Patent
Bodas et al.

(10) Patent No.: US 12,623,987 B2
(45) Date of Patent: May 12, 2026

(54) REMOVAL OF C3 LIGHTS FROM LPG FEEDSTOCK TO BUTANE ISOMERIZATION UNIT

(71) Applicant: SABIC GLOBAL TECHNOLOGIES B.V., Bergen Op Zoom (NL)

(72) Inventors: Vijay Dinkar Bodas, Riyadh (SA); Guillermo Leal Canelon, Riyadh (SA); Mohammed Bismillah Ansari, Riyadh (SA)

(73) Assignee: SABIC Global Technologies B.V., Bergen op Zoom (NL)

( * ) Notice: Subject to any disclaimer, the term of this patent is extended or adjusted under 35 U.S.C. 154(b) by 576 days.

(21) Appl. No.: 18/005,592

(22) PCT Filed: Jul. 16, 2021

(86) PCT No.: PCT/IB2021/056455
§ 371 (c)(1),
(2) Date: Jan. 13, 2023

(87) PCT Pub. No.: WO2022/013836
PCT Pub. Date: Jan. 20, 2022

(65) Prior Publication Data
US 2023/0265033 A1 Aug. 24, 2023

(30) Foreign Application Priority Data
Jul. 17, 2020 (EP) .................................... 20186357

(51) Int. Cl.
| | |
|---|---|
| *C07C 41/06* | (2006.01) |
| *C07C 4/04* | (2006.01) |
| *C07C 5/27* | (2006.01) |
| *C07C 5/333* | (2006.01) |

(52) U.S. Cl.
CPC ................ *C07C 41/06* (2013.01); *C07C 4/04* (2013.01); *C07C 5/2754* (2013.01); *C07C 5/3335* (2013.01); *C07C 5/3337* (2013.01); *C07C 2521/04* (2013.01); *C07C 2521/06* (2013.01); *C07C 2523/26* (2013.01); *C07C 2523/42* (2013.01)

(58) Field of Classification Search
CPC ......... C07C 5/2724; C07C 9/12; C07C 5/333; C07C 11/06; C07C 5/42; C07C 11/09; C07C 5/3335; C07C 5/3337; C07C 41/06; C07C 43/046; C07C 7/04; C07C 9/08; C07C 9/10; C07C 4/04; C07C 11/04

USPC .......................................................... 568/637
See application file for complete search history.

(56) References Cited

U.S. PATENT DOCUMENTS

| | | | |
|---|---|---|---|
| 4,393,250 | A | 7/1983 | Gottlieb et al. |
| 4,503,264 | A | 3/1985 | Al-Muddarris |
| 4,546,204 | A | 10/1985 | Parris |
| 4,695,662 | A | 9/1987 | Vora |
| 5,105,024 | A | 4/1992 | Mckay et al. |
| 7,034,195 | B2 | 4/2006 | Schindler et al. |
| 7,193,121 | B2 | 3/2007 | Walsdorff et al. |
| 10,053,440 | B2 | 8/2018 | Bolz et al. |
| 2009/0112031 | A1 | 4/2009 | Eng |
| 2018/0002300 | A1 | 1/2018 | Bolz et al. |

FOREIGN PATENT DOCUMENTS

| | | |
|---|---|---|
| AU | 563178 | 7/1987 |
| CN | 105037108 | 11/2015 |
| CN | 104250192 | 3/2016 |
| EP | 820975 B1 | 3/2001 |
| JP | 06067014 | 1/2017 |

OTHER PUBLICATIONS

European Search Report issued in corresponding European Application No. 20196357.8, dated Jan. 12, 2021.
International Search Report and Written Opinion issued in corresponding International application PCT/IB2021/056455 mailed Oct. 8, 2021.
Office Action issued in corresponding Chinese Application No. 202180060654.1, dated Feb. 28, 2025 (English Translation provided).
Zhou, Hong. "Comprehensive Utilization of Light Hydrocarbon and Dry Gas in Refinery." *Qilu Petrochemical Technology*, vol. 47, No. 1, 2019, pp. 75-80 (English Abstract provided).

*Primary Examiner* — Ana Z Muresan
(74) *Attorney, Agent, or Firm* — Norton Rose Fulbright US LLP

(57) ABSTRACT

Systems and methods for processing a $C_3$ and $C_4$ hydrocarbon mixture have been disclosed. The $C_3$ and $C_4$ hydrocarbon mixture is first processed in an isomerization unit to isomerize n-butane to form isobutane. The resulting effluent stream from the isomerization unit comprising primarily isobutane and $C_3$ hydrocarbons, collectively, is flowed into a separation unit configured to separate the effluent stream to form a $C_3$ stream comprising $C_1$ to $C_3$ hydrocarbons and a $C_4$ stream comprising primarily isobutane. The isobutane in the $C_4$ stream is further dehydrogenated to form isobutene, which is further flowed into an MTBE synthesis unit as a feedstock for producing MTBE.

17 Claims, 2 Drawing Sheets

200

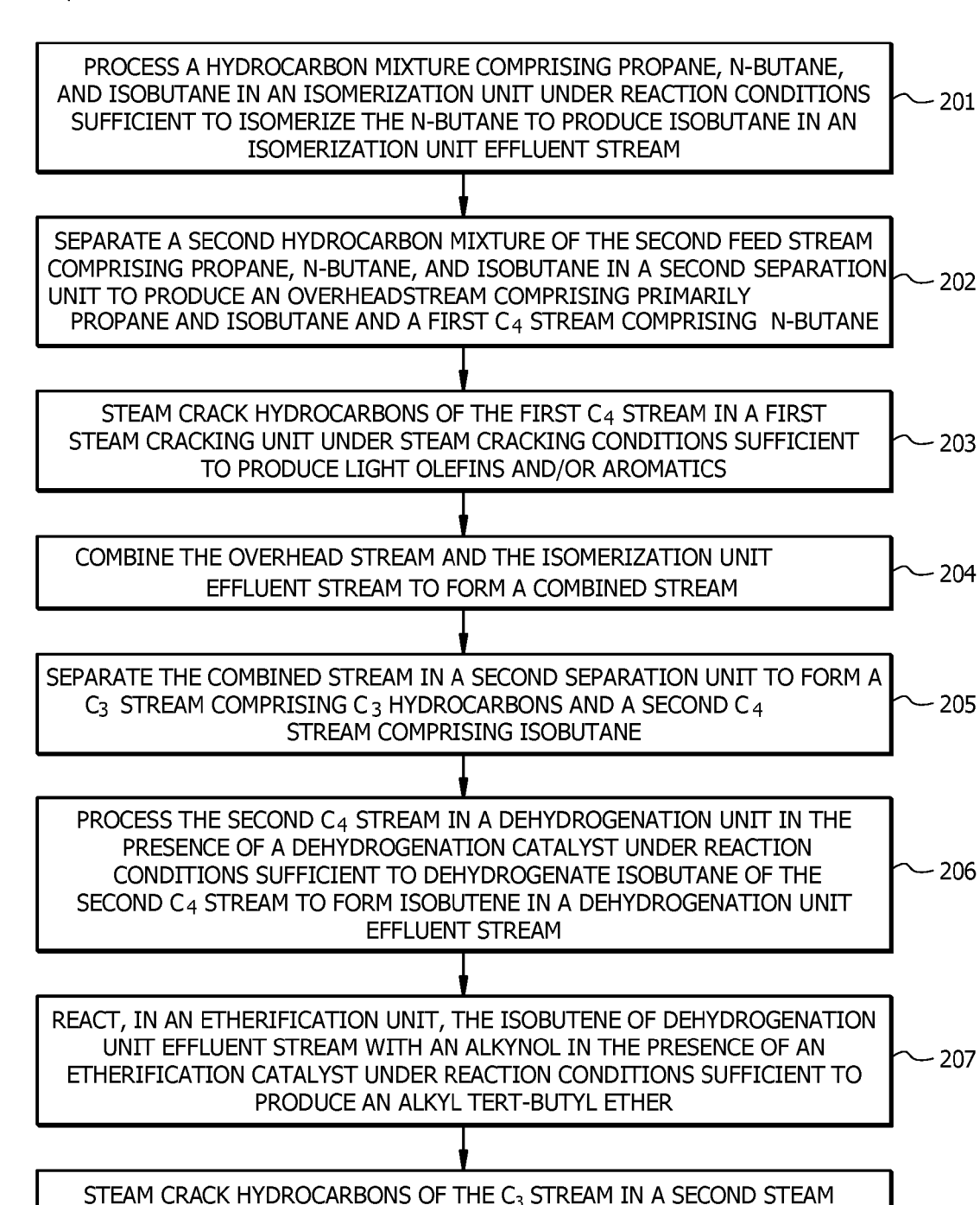

PROCESS A HYDROCARBON MIXTURE COMPRISING PROPANE, N-BUTANE, AND ISOBUTANE IN AN ISOMERIZATION UNIT UNDER REACTION CONDITIONS SUFFICIENT TO ISOMERIZE THE N-BUTANE TO PRODUCE ISOBUTANE IN AN ISOMERIZATION UNIT EFFLUENT STREAM ⁓ 201

SEPARATE A SECOND HYDROCARBON MIXTURE OF THE SECOND FEED STREAM COMPRISING PROPANE, N-BUTANE, AND ISOBUTANE IN A SECOND SEPARATION UNIT TO PRODUCE AN OVERHEADSTREAM COMPRISING PRIMARILY PROPANE AND ISOBUTANE AND A FIRST $C_4$ STREAM COMPRISING N-BUTANE ⁓ 202

STEAM CRACK HYDROCARBONS OF THE FIRST $C_4$ STREAM IN A FIRST STEAM CRACKING UNIT UNDER STEAM CRACKING CONDITIONS SUFFICIENT TO PRODUCE LIGHT OLEFINS AND/OR AROMATICS ⁓ 203

COMBINE THE OVERHEAD STREAM AND THE ISOMERIZATION UNIT EFFLUENT STREAM TO FORM A COMBINED STREAM ⁓ 204

SEPARATE THE COMBINED STREAM IN A SECOND SEPARATION UNIT TO FORM A $C_3$ STREAM COMPRISING $C_3$ HYDROCARBONS AND A SECOND $C_4$ STREAM COMPRISING ISOBUTANE ⁓ 205

PROCESS THE SECOND $C_4$ STREAM IN A DEHYDROGENATION UNIT IN THE PRESENCE OF A DEHYDROGENATION CATALYST UNDER REACTION CONDITIONS SUFFICIENT TO DEHYDROGENATE ISOBUTANE OF THE SECOND $C_4$ STREAM TO FORM ISOBUTENE IN A DEHYDROGENATION UNIT EFFLUENT STREAM ⁓ 206

REACT, IN AN ETHERIFICATION UNIT, THE ISOBUTENE OF DEHYDROGENATION UNIT EFFLUENT STREAM WITH AN ALKYNOL IN THE PRESENCE OF AN ETHERIFICATION CATALYST UNDER REACTION CONDITIONS SUFFICIENT TO PRODUCE AN ALKYL TERT-BUTYL ETHER ⁓ 207

STEAM CRACK HYDROCARBONS OF THE $C_3$ STREAM IN A SECOND STEAM CRACKING UNIT UNDER CONDITIONS SUFFICIENT TO PRODUCE LIGHT OLEFINS AND/OR AROMATICS ⁓ 208

FIG. 2

REMOVAL OF C3 LIGHTS FROM LPG FEEDSTOCK TO BUTANE ISOMERIZATION UNIT

CROSS REFERENCE TO RELATED APPLICATIONS

This application is a national phase under 35 U.S.C. § 371 of International Application No. PCT/IB2021/056455, filed Jul. 16, 2021, which claims the benefit of priority to European Patent Application No. 20186357.8, filed Jul. 17, 2020, the entire contents of which are hereby incorporated by reference in their entirety.

FIELD OF INVENTION

The present invention generally relates to a process of producing alkyl tert-butyl ether. More specifically, the present invention relates to a process of producing alkyl tert-butyl ether using liquefied petroleum gas as a feedstock.

BACKGROUND OF THE INVENTION

MTBE is an organic compound that is used as an additive in gasoline to enhance the octane number of the gasoline. Since about 1970, MTBE has been synthesized by etherification of isobutylene by reaction with methanol in the presence of an acidic catalyst. Isobutylene used for MTBE synthesis can be obtained from $C_4$ hydrocarbons. Generally, isobutylene and methanol are fed into a fixed bed reactor to produce an MTBE containing effluent. The effluent is then fed to a reaction column to react isobutylene remaining in the effluent with additional methanol to produce more MTBE.

One of the sources for the $C_4$ hydrocarbons used in the MTBE production process can include liquefied petroleum gas, which includes primarily $C_4$ and $C_3$ hydrocarbons. The liquefied petroleum gas is processed in an isomerization unit and then by a dehydrogenation unit to produce isobutylene. The effluent stream from the dehydrogenation unit(s) is then flowed to an MTBE synthesis unit to react with methanol for producing MTBE. However, the reaction efficiency in the isomerization unit(s) and/or dehydrogenation unit(s) is relatively low when liquefied petroleum gas is used as the feedstock, resulting in high production cost for MTBE.

Overall, while systems and methods for producing MTBE from a $C_4$ and $C_3$ hydrocarbon mixture (e.g., liquefied petroleum gas) exist, the need for improvements in this field persists in light of at least the aforementioned drawback for the conventional systems and methods.

BRIEF SUMMARY OF THE INVENTION

A solution to at least the above mentioned problem associated with the systems and methods for producing MTBE from a $C_4$ and $C_3$ hydrocarbon mixture (e.g., liquefied petroleum gas) has been discovered. The solution resides in a method for processing a hydrocarbon mixture that includes $C_4$ and $C_3$ hydrocarbons. The method includes processing the hydrocarbon mixture in an isomerization unit to produce isobutane, separating an effluent from the isomerization unit to form a $C_3$ stream comprising propane and a $C_4$ stream comprising isobutane, and dehydrogenating the isobutane, in the $C_4$ stream, in a dehydrogenation unit, to produce isobutene. An effluent from the dehydrogenation unit is further flowed into an etherification unit for producing alkyl tert-butyl ether. This can be beneficial for at least reducing the inert portion in the feed stream flowed into the isomerization unit and/or the dehydrogenation unit, thereby increasing the reaction efficiency for dehydrogenating isobutane. Furthermore, the disclosed method can reduce or eliminate the large amount of propane in the effluent stream of the dehydrogenation unit, resulting in a feed stream with higher concentration of isobutene being flowed into the MTBE synthesis unit. Hence, the disclosed method is capable of increasing the reaction efficiency in the etherification unit, and reducing the amount of gas that is recycled back to the dehydrogenation unit, resulting in reduced production cost for alkyl tert-butyl ether. Therefore, the systems and methods of the present invention provide a technical solution to at least some of the problems associated with the conventional systems and methods for alkyl tert-butyl ether production as mentioned above.

Embodiments of the invention include a method of processing a hydrocarbon mixture. The method comprises processing a hydrocarbon mixture comprising propane, n-butane, and isobutane in an isomerization unit under reaction conditions sufficient to isomerize the n-butane to produce isobutane and form an isomerization unit effluent comprising propane, isobutane, or combinations thereof. The method further comprises separating the isomerization unit effluent to form a $C_3$ stream comprising propane and a $C_4$ stream comprising isobutane. The method further comprises steam cracking the propane of the $C_3$ stream under reaction conditions sufficient to produce propylene. The method further comprises dehydrogenating the isobutane of the $C_4$ stream in a dehydrogenation unit to produce isobutene in a dehydrogenation unit effluent. The method further comprises reacting, in an etherification unit, the isobutene of the dehydrogenation unit effluent with an alkanol in the presence of an etherification catalyst under reaction conditions sufficient to produce alkyl tert-butyl ether in an etherification unit effluent.

Embodiments of the invention include a method of processing a hydrocarbon mixture. The method comprises processing a hydrocarbon mixture comprising propane, n-butane, and isobutane in an isomerization unit under reaction conditions sufficient to isomerize the n-butane to produce isobutane and form an isomerization unit effluent comprising propane, isobutane, or combinations thereof. The method comprises separating a second hydrocarbon mixture comprising propane, n-butane, and isobutane in a second separation unit to produce an overhead stream comprising primarily propane and isobutane, collectively, and a first $C_4$ stream comprising primarily n-butane. The method comprises combining the overhead stream and the isomerization unit effluent to form a combined stream. The method comprises separating the combined stream to form a $C_3$ stream comprising primarily propane and a second $C_4$ stream comprising isobutane. The method comprises dehydrogenating the isobutane of the second $C_4$ stream in a dehydrogenation unit to produce isobutene in a dehydrogenation unit effluent. The method comprises reacting, in an etherification unit, the isobutene of the dehydrogenation unit effluent with an alkanol in the presence of an etherification catalyst under reaction conditions sufficient to produce alkyl tert-butyl ether in an etherification effluent.

Embodiments of the invention include a method of processing a hydrocarbon mixture. The method comprises processing a hydrocarbon mixture comprising propane, n-butane, and isobutane in an isomerization unit under reaction conditions sufficient to isomerize the n-butane to produce isobutane and form an isomerization unit effluent comprising propane, isobutane, or combinations thereof. The method comprises separating a second hydrocarbon mixture comprising propane, n-butane, and isobutane in a second separation unit to produce an overhead stream comprising primarily propane and isobutane, collectively, and a first $C_4$ stream comprising primarily n-butane. The method comprises steam-cracking the first $C_4$ stream to produce olefins and/or aromatics. The method comprises combining the overhead stream and the isomerization unit effluent to form a combined stream. The method comprises separating the combined stream to form a $C_3$ stream comprising primarily propane and a second $C_4$ stream comprising isobutane. The method comprises steam-cracking the second $C_3$ stream to produce olefins and/or aromatics. The method comprises dehydrogenating the isobutane of the second $C_4$ stream in a dehydrogenation unit to produce isobutene in a dehydrogenation unit effluent. The method comprises reacting, in an etherification unit, the isobutene of the dehydrogenation unit effluent with methanol in the presence of an etherification catalyst under reaction conditions sufficient to produce methyl tert-butyl ether in an etherification effluent.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, include any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which:

FIG. 2 shows a schematic flowchart of a method for producing MTBE, according to embodiments of the invention.

DETAILED DESCRIPTION OF THE INVENTION

Figure 1:
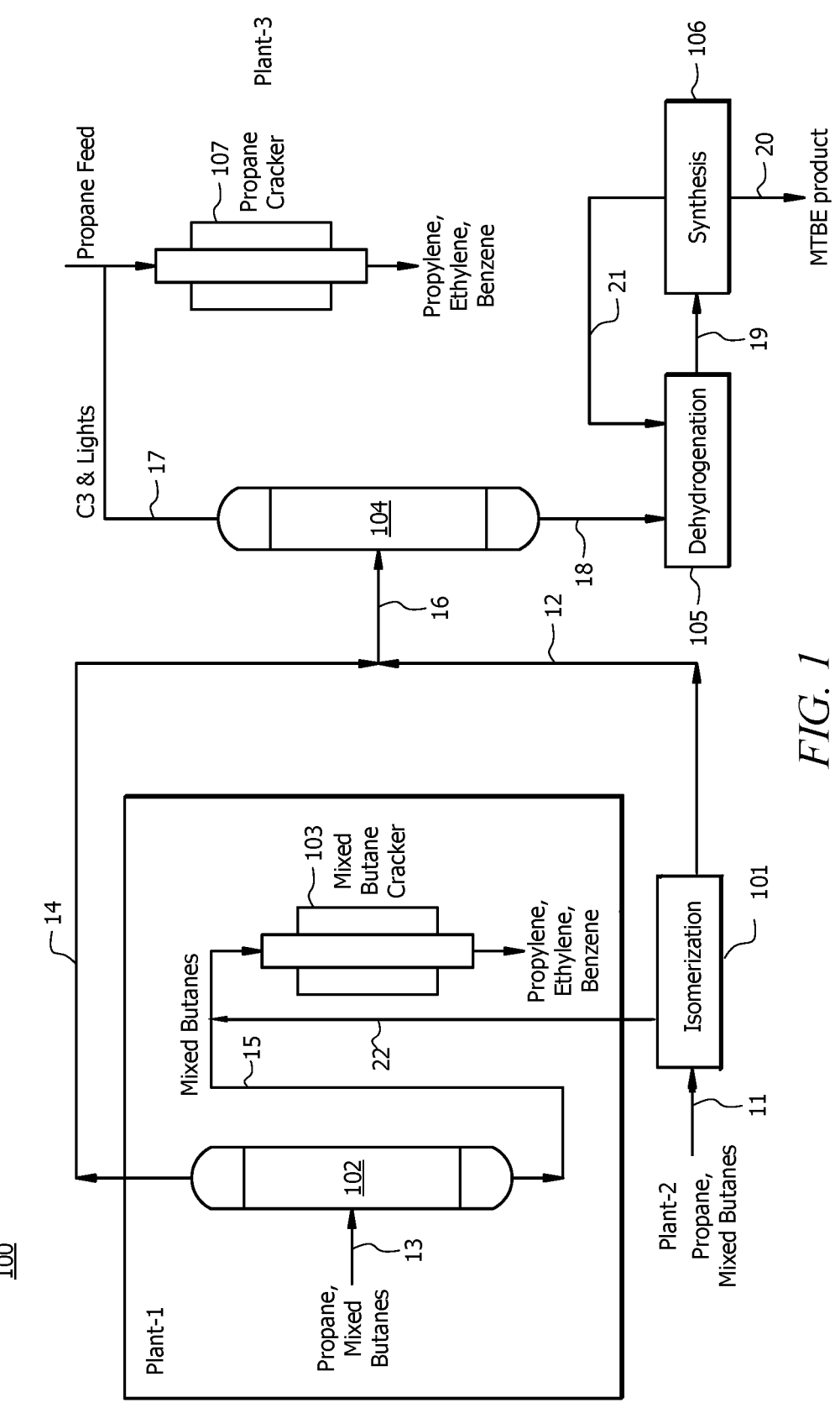
FIG. 1 shows a schematic diagram of a system for producing MTBE, according to embodiments of the invention.

Currently, MTBE can be produced by processing a $C_3$ and $C_4$ hydrocarbon mixture in an isomerization unit and a dehydrogenation unit, sequentially. The effluent from the dehydrogenation unit comprising isobutene is then fed into a MTBE synthesis unit to produce MTBE. However, the $C_3$ hydrocarbons and lighter hydrocarbons (e.g., methane and $C_2$ hydrocarbons) in the hydrocarbon mixture are inert components that dilute the $C_4$ hydrocarbon reactants in each of the reaction units, thereby reducing the reaction efficiency and increasing the energy consumption for producing MTBE. The present invention provides a solution to the problem. The solution is premised on a system and a method for processing hydrocarbons that includes separating $C_3$ and/or $C_1$ to $C_2$ hydrocarbons from the hydrocarbon mixture before it is processed in a dehydrogenation unit, resulting in higher isobutane concentration and consequently higher reaction efficiency in the feed stream for the dehydrogenation unit, compared to conventional methods. Moreover, the separated $C_3$ and/or $C_1$ to $C_2$ hydrocarbons can be processed in a steam cracking unit for producing light olefins and/or aromatics, thereby increasing the utilization rate and the overall value of the $C_3$ and $C_4$ hydrocarbon mixture. These and other non-limiting aspects of the present invention are discussed in further detail in the following sections.

A. System for Processing $C_3$ and $C_4$ Hydrocarbon Mixture

In embodiments of the invention, the system for processing a hydrocarbon mixture comprising $C_3$ and $C_4$ hydrocarbons includes an isomerization unit, a separation unit, a dehydrogenation unit, a steam cracking unit, and a MTBE synthesis unit. Notably, the system is capable of reducing energy consumption and increasing efficiency for producing MTBE, compared to conventional systems. With reference to FIG. 1, a schematic diagram is shown for system 100, which is used for producing MTBE using a $C_3$ and $C_4$ mixture as a feedstock.

According to embodiments of the invention, system 100 comprises isomerization unit 101. Isomerization unit 101 can be configured to isomerize at least some n-butane of first feed stream 11 to produce isobutane. In embodiments of the invention, first feed stream 11 includes a mixture of $C_3$ and $C_4$ hydrocarbons. First feed stream 11 may further include methane and $C_2$ hydrocarbons. According to embodiments of the invention, first feed stream 11 is a liquefied petroleum gas stream. First feed stream 11 may include 0 to 7 wt. % propane, 60 to 80 wt. % isobutane and 20 to 30 wt. % n-butane. Isomerization unit 101, according to embodiments of the invention, can be further configured to separate unreacted n-butane from isobutane to produce isomerization unit effluent stream 12 comprising primarily isobutane and $C_3$ hydrocarbons. Isomerization unit 101 may include a fixed bed reactor, a continuous catalytic converter, and/or an adiabatic or a cooled isothermal converter. Isomerization unit 101, in embodiments of the invention, comprises a catalyst including $Pt/AlCl_3/Al_2O_3$, $Pt/AlCl_3$/zeolite, $Pt/SO_4^{2-}$—$ZrO_2$, $SO_4^{2-}/ZrO_2$—$Al_2O_3$, or any combination thereof. In embodiments of the invention, isomerization unit 101 further includes a de-isobutanizer configured to separate isobutane and $C_3$ hydrocarbons from unreacted n-butane to produce unreacted n-butane stream 22 comprising primarily n-butane and isomerization unit effluent stream 12 comprising primarily isobutane.

According to embodiments of the invention, system 100 comprises first separation unit 102 configured to separate second feed stream 13 comprising a mixture of $C_3$ and $C_4$ hydrocarbons to form overhead stream 14 comprising one or more $C_3$ hydrocarbons and isobutane, and first $C_4$ stream 15 comprising primarily n-butane. Second feed stream 13 may have substantially the same composition as first feed stream 11. First separation unit 102 may include a distillation column. The distillation column may be a de-isobutanizer. In embodiments of the invention, overhead stream 14 further comprises methane and/or one or more $C_2$ hydrocarbons. In embodiments of the invention, an outlet of first separation unit 102 is in fluid communication with an inlet of first steam cracking unit 103 such that first $C_4$ stream 15 flows from first separation unit 102 to first steam cracking unit 103. First steam cracking unit 103 can be configured to steam crack hydrocarbons including n-butane of first $C_4$ stream 15 to produce (1) light olefins comprising propylene and ethylene, and/or (2) aromatics comprising benzene. In embodiments of the invention, an outlet of isomerization unit 101 is in fluid communication with an inlet of first steam cracking unit 103 such that unreacted n-butane stream 22 flows from isomerization unit 101 to first steam cracking unit 103. In addition to, or as an alternative to flowing to first steam cracking unit 103, unreacted n-butane stream 22 may be combined with first $C_4$ stream 15 before it is flowed into first steam cracking unit 103.

According to embodiments of the invention, an outlet of isomerization unit 101 may be in fluid communication with an inlet of second separation unit 104. An outlet of first separation unit 102 may be in fluid communication with an inlet of second separation unit 104. First overhead stream 14 and isomerization unit effluent stream 12, in embodiments of the invention, may be combined to form combined stream 16, which is fed into second separation unit 104. As an alternative to combining overhead stream 14 and isomerization unit effluent stream 12, overhead stream 14 and isomerization unit effluent stream 12 can be flowed into second separation unit 104 separately. Second separation unit 104 may be configured to separate combined stream 16 or isomerization unit effluent stream 12 to form $C_3$ stream 17 comprising one or more $C_3$ hydrocarbons and second $C_4$ stream 18 comprising primarily isobutane. In embodiments of the invention, second separation unit 104 includes a depropanizer. $C_3$ stream 17 may further include $C_1$ to $C_2$ hydrocarbons. In embodiments of the invention, an outlet of second separation unit 104 is in fluid communication with second steam cracking unit 107 such that $C_3$ stream 17 flows from second separation unit 104 to second steam cracking unit 107. Second steam cracking unit 107 may include a propane steam cracker configured to crack hydrocarbons of $C_3$ stream 17 to produce light olefins (e.g., ethylene and propylene) and/or aromatics (e.g., benzene).

According to embodiments of the invention, an outlet of second separation unit 104 is in fluid communication with dehydrogenation unit 105 such that second $C_4$ stream 18 is flowed from second separation unit 104 to dehydrogenation unit 105. Dehydrogenation unit 105 is configured to dehydrogenate isobutane of second $C_4$ stream 18 to produce isobutene in dehydrogenation unit effluent stream 19. Dehydrogenation unit effluent stream 19 may further include unreacted isobutane. In embodiments of the invention, dehydrogenation unit 105 includes one or more fixed bed reactors, one or more fluidized bed reactors, and/or one or more continuous catalytic converters. Dehydrogenation unit 105 may include a dehydrogenation catalyst comprising chromia/alumina, Pt/alumina, or any combination thereof.

According to embodiments of the invention, an outlet of dehydrogenation unit 105 may be in fluid communication with an inlet of etherification unit 106 such that dehydrogenation unit effluent stream 19 is flowed to etherification unit 106. In embodiments of the invention, etherification unit 106 is configured to react isobutene of dehydrogenation unit effluent stream 19 with methanol under reaction conditions sufficient to produce product stream 20 comprising MTBE and recycle stream 21 comprising isobutane. Etherification unit 106 may comprise an MTBE synthesis reactor and/or an ethyl tert-butyl ether (ETBE) synthesis reactor, and an effluent separator configured to separate an effluent from the MTBE synthesis reactor to form product stream 20 and recycle stream 21. The MTBE and/or ETBE synthesis reactor can include a catalyst for catalyzing MTBE and/or ETBE synthesis reaction including cation exchange resin, sulfonated styrene divinyl benzene, polystyrene polymer mounted cation exchange resin, or combinations thereof. In embodiments of the invention, an outlet of etherification unit 106 is in fluid communication with an inlet of dehydrogenation unit 105 such that recycle stream 21 is flowed back to dehydrogenation unit 105.

According to embodiments of the invention, first separation unit 102 and first steam cracking unit 103 are part of plant 1, which can include a mixed butanes cracker. Isomerization unit 101, second separation unit 104, dehydrogenation unit 105, and etherification unit 106 can be part of plant 2, which can include a MTBE synthesis plant. In embodiments of the invention, second steam cracking unit 107 can be a part of plant 3, which includes a propane cracking unit.

B. Method of Processing $C_3$ and $C_4$ Hydrocarbon Mixture

Methods of processing a $C_3$ and $C_4$ hydrocarbon mixture have been discovered. As shown in FIG. 2, embodiments of the invention include method 200 for processing a $C_3$ and $C_4$ hydrocarbon mixture for producing MTBE with improved efficiency and reduced energy consumption compared to conventional methods. Method 200 may be implemented by system 100, as shown in FIG. 1 and described above.

According to embodiments of the invention, as shown in block 201, method 200 includes processing a hydrocarbon mixture of first feed stream 11 comprising propane, n-butane, and isobutane in isomerization unit 101 under reaction conditions sufficient to isomerize the n-butane to produce isobutane in isomerization unit effluent stream 12. In embodiments of the invention, processing at block 201 can include reacting n-butane of first feed stream 11 in a reactor of isomerization unit 101 to produce isobutane, and separating mixture from the reactor of isomerization unit 101 by a de-isobutanizer of isomerization unit 101 to produce isomerization unit effluent stream 12 and unreacted n-butane stream 22. First feed stream 11 may include 0 to 7 wt. % propane, 60 to 80 wt. % isobutane and 20 to 30 wt. % n-butane. First feed stream 11 may further include methane and/or $C_2$ hydrocarbons. In embodiments of the invention, first feed stream 11 includes liquefied petroleum gas. Isomerization unit effluent stream 12 may comprise propane, isobutane, or any combination thereof. Isomerization unit effluent stream 12 may comprise 95 to 99.5 wt. % isobutane and all ranges and values there between including ranges of 95 to 95.5 wt. %, 95.5 to 96 wt. %, 96 to 96.5 wt. %, 96.5 to 97 wt. %, 97 to 97.5 wt. %, 97.5 to 98 wt. %, 98 to 98.5 wt. %, 98.5 to 99 wt. %, and 99 to 99.5 wt. %.

The reaction conditions in the reactor of isomerization unit 101, at block 201, can include a reaction temperature of 125 to 175° C. and all ranges and values there between. The reaction conditions in isomerization unit 101 at block 201 may further include a reaction pressure of 20 to 30 bar and all ranges and values there between. The reaction conditions in isomerization unit 101 at block 201 may further still include a weight hourly space velocity in a range of 4 to 6 $hr^{-1}$ and all ranges and values there between.

According to embodiments of the invention, as shown in block 202, method 200 includes separating a second hydrocarbon mixture of second feed stream 13 comprising propane, n-butane, and isobutane in first separation unit 102 to produce overhead stream 14 comprising primarily propane and isobutane, collectively and first $C_4$ stream 15 comprising n-butane. In embodiments of the invention, second feed stream 13 comprises 0 to 7 wt. % propane, 60 to 80 wt. % isobutane and 20 to 30 wt. % n-butane. Second feed stream 13 may further include methane and/or $C_2$ hydrocarbons. Second feed stream 13, according to embodiments of the invention, includes liquefied petroleum gas.

In embodiments of the invention, first separation unit 102 includes a distillation column. The distillation column may be operated at an overhead dew point range of 40 to 55° C., a bottom temperature range of 60 to 90° C., and an operating pressure of 7 to 8.5 bar. Overhead stream 14 may comprise 0 to 21 wt. % propane and 79 to 100 wt. % isobutane. According to embodiments of the invention, as shown in block 203, method 200 includes steam cracking hydrocarbons of first $C_4$ stream 15 in first steam cracking unit 103 under steam cracking conditions sufficient to produce light olefins and/or aromatics. Non-limiting examples of light olefins can include propylene and ethylene. Non-limiting examples of aromatics can include benzene. At block 203, first steam cracking unit 103 may be operated at a temperature of 750 to 890° C. and a residence time of 0.1 to 0.5 s. In embodiments of the invention, unreacted n-butane stream 22 is flowed into first steam cracking unit 103 and the n-butane of unreacted n-butane stream 22 is steam cracked to produce light olefins and/or aromatics.

According to embodiments of the invention, as shown in block 204, method 200 includes combining overhead stream 14 and isomerization unit effluent stream 12 to form combined stream 16. According to embodiments of the invention, as shown in block 205, method 200 includes separating combined stream 16 in second separation unit 104 to form $C_3$ stream 17 comprising primarily $C_3$ hydrocarbons and second $C_4$ stream 18 comprising primarily isobutane. As an alternative to combining overhead stream 14 and isomerization unit effluent stream 12, overhead stream 14 and isomerization unit effluent stream 12 can be separately flowed into second separation unit 104, and then separated to produce $C_3$ stream 17 and second $C_4$ stream 18. In embodiments of the invention, $C_3$ stream 17 further comprises $C_1$ and $C_2$ hydrocarbons. Second $C_4$ stream 18 may comprise 97 to 99 wt. % isobutane. Second separation unit 104 may include a distillation column. The distillation column may be operated at an overhead dew point range of 40 to 55° C., a bottom temperature range of 90 to 95° C., and an operating pressure of 17 to 19 bar. In embodiments of the invention, separating of overhead stream 14 and isomerization unit effluent stream 12 in second separation unit 104 is configured to increase the purity of the isobutane fed into dehydrogenation unit 105, thereby increasing the efficiency of dehydrogenation unit 105 and MTBE synthesis unit 106 by reducing inert portions of feedstocks.

According to embodiments of the invention, as shown in block 206, method 200 includes processing second $C_4$ stream 18 in dehydrogenation unit 105 in the presence of the dehydrogenation catalyst under dehydrogenation conditions sufficient to dehydrogenate isobutane of second $C_4$ stream 18 to form isobutene in dehydrogenation unit effluent stream 19. In embodiments of the invention, the dehydrogenation conditions at block 206 include a temperature of 520 to 640° C., a pressure of 0.36 to 1.2 bar, and a weight hourly space velocity in a range of 0.2 to 1.2 $hr^{-1}$. Dehydrogenation unit effluent stream 19 may include 35 to 65 wt. % isobutene and all ranges and values there between including ranges of 35 to 40 wt. %, 40 to 45 wt. %, 45 to 50 wt. %, 50 to 55 wt. %, 55 to 60 wt. %, and 60 to 65 wt. %.

According to embodiments of the invention, as shown in block 207, method 200 includes reacting, in etherification unit 106, the isobutene of dehydrogenation unit effluent stream 19 with an alkanol in the presence of an etherification catalyst under reaction conditions sufficient to produce an alkyl tert-butyl ether. In embodiments of the invention, non-limiting examples of the alkanol include methanol and ethanol. Non-limiting examples of the alkyl tert-butyl ether may include MTBE and ethyl tert-butyl ether. The etherification catalyst may comprise a cation exchange resin, a poly Styrene divinyl benzene mounted ion exchange resin, a polymeric support mounted ion exchange resin, or combinations thereof. The reaction conditions in etherification unit 106, at block 207, may include an etherification temperature of 40 to 45° C., an etherification pressure of 5 to 8 bar, and a liquid hourly space velocity of 0.5 to 3.5 $hr^{-1}$. In embodiments of the invention, etherification unit 106 is configured to produce product stream 20 including 98 to 99.5 wt. % MTBE and recycle stream 21 comprising isobutane.

According to embodiments of the invention, as shown in block 208, method 200 includes steam-cracking hydrocarbons of $C_3$ stream 17 in second steam cracking unit 107 under conditions sufficient to produce light olefins and/or aromatics. Non-limiting examples of light olefins produced at block 208 can include propylene, and ethylene. Non-limiting examples of aromatics produced at block 208 can include benzene. At block 208, second steam cracking unit 107 may be operated at a temperature of 750 to 890° C. and a residence time of 0.1 to 0.5 s.

In embodiments of the invention, the cracking of first $C_4$ stream 15 and/or unreacted n-butane stream 22 at block 203, and/or the cracking of $C_3$ stream 17 at block 208 are configured to produce propylene and other high value chemicals including ethylene and benzene, thereby improving the overall product value and offsetting costs for dehydrogenation unit 105 and etherification unit 106, resulting in improved efficiency for system 100.

Although embodiments of the present invention have been described with reference to blocks of FIG. 2, it should be appreciated that operation of the present invention is not limited to the particular blocks and/or the particular order of the blocks illustrated in FIG. 2. Accordingly, embodiments of the invention may provide functionality as described herein using various blocks in a sequence different than that of FIG. 2.

The systems and processes described herein can also include various equipment that is not shown and is known to one of skill in the art of chemical processing. For example, some controllers, piping, computers, valves, pumps, heaters, thermocouples, pressure indicators, mixers, heat exchangers, and the like may not be shown.

As part of the disclosure of the present invention, specific examples are included below. The examples are for illustrative purposes only and are not intended to limit the invention. Those of ordinary skill in the art will readily recognize parameters that can be changed or modified to yield essentially the same results.

In the context of the present invention, at least the following 17 embodiments are described. Embodiment 1 is a method of processing a hydrocarbon mixture. The method includes processing a hydrocarbon mixture containing propane, n-butane, and isobutane in an isomerization unit under reaction conditions sufficient to isomerize the n-butane to produce isobutane and form an isomerization unit effluent containing propane, isobutane, or combinations thereof. The method further includes separating the isomerization unit effluent to form a $C_3$ stream containing propane and a $C_4$ stream containing isobutane. The method still further includes cracking the propane of the $C_3$ stream under reaction conditions sufficient to produce propylene. The method also includes dehydrogenating the isobutane of the $C_4$ stream in a dehydrogenation unit to produce isobutene in a dehydrogenation unit effluent. In addition, the method includes reacting, in an etherification unit, the isobutene of the dehydrogenation unit effluent with an alkanol in the presence of a catalyst under reaction conditions sufficient to produce alkyl tert-butyl ether in a product stream.

Embodiment 2 is a method of processing a hydrocarbon mixture. The method includes processing a first hydrocarbon mixture containing propane, n-butane, and isobutane in an isomerization unit under reaction conditions sufficient to isomerize the n-butane to produce isobutane and form an isomerization unit effluent containing propane, isobutane, or combinations thereof. The method further includes separating a second hydrocarbon mixture containing propane, n-butane, and isobutane in a second separation unit to produce an overhead stream containing primarily propane and isobutane, collectively, and a first $C_4$ stream containing n-butane and isobutane. The method still further includes combining the overhead stream and the isomerization unit effluent to form a combined stream and separating the combined stream to form a $C_3$ stream containing primarily propane and a second $C_4$ stream containing isobutane. The method also includes dehydrogenating the isobutane of the second $C_4$ stream in a dehydrogenation unit to produce isobutene in a dehydrogenation unit effluent, and reacting, in an etherification unit, the isobutene of the dehydrogenation unit effluent with an alkanol in the presence of a catalyst under reaction conditions sufficient to produce an alkyl tert-butyl ether in a product stream. Embodiment 3 is the method of embodiment 2, further including steam-cracking the $C_3$ stream in a first steam cracking unit. Embodiment 4 is the method of embodiment 3, wherein the steam cracking of the second $C_3$ stream is performed at a temperature of 750 to 900° C. and a steam cracker residence time of 0.1 to 0.5 s. Embodiment 5 is the method of any of embodiments 2 to 4, further including steam-cracking the first $C_4$ stream in a second steam cracking unit. Embodiment 6 is the method of any of embodiments 2 to 5, wherein the isomerization unit includes an isomerization catalyst containing $Pt/AlCl_3/Al_2O_3$, $Pt/AlCl_3/zeolite$, $Pt/SO_4^{2-}—ZrO_2$, $SO_4^{2-}/ZrO_2—Al_2O_3$, or combinations thereof. Embodiment 7 is the method of any of embodiments 2 to 6, wherein the reaction conditions in the isomerization unit include an isomerization temperature of 125 to 175° C. Embodiment 8 is the method of any of embodiments 2 to 7, wherein the reaction conditions in the isomerization unit include an isomerization pressure of 20 to 30 bar. Embodiment 9 is the method of any of embodiments 2 to 8, wherein the isomerization unit effluent contains 95 to 99.5 wt. % isobutane. Embodiment 10 is the method of any of embodiments 2 to 9, wherein the dehydrogenation unit effluent contains 35 to 65 wt. % isobutene. Embodiment 11 is the method of any of embodiments 2 to 10, wherein the first hydrocarbon mixture and/or the second hydrocarbon mixture contain liquefied petroleum gas. Embodiment 12 is the method of any of embodiments 2 to 11, wherein the first hydrocarbon mixture contains 60 to 80 wt. % n-butane and 20 to 30 wt. % isobutane. Embodiment 13 is the method of any of embodiments 2 to 12, wherein the etherification unit further produces a recycle stream containing isobutane. Embodiment 14 is the method of embodiment 13 further including flowing the recycle stream into the dehydrogenation unit. Embodiment 15 is the method of any of embodiments 2 to 14, wherein the dehydrogenation unit includes a dehydrogenation catalyst containing chromia/alumina, Pt/alumina, or combinations thereof. Embodiment 16 is the method of any of embodiments 2 to 15, wherein the alkanol contains methanol, ethanol, or combinations thereof. Embodiment 17 is the method of embodiment 16, wherein alkyl tert-butyl ether contains MTBE, ETBE, or combinations thereof.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of processing a hydrocarbon mixture, the method comprising:
    processing a first hydrocarbon mixture comprising propane, n-butane, and isobutane in an isomerization unit at a temperature of 125 to 175° C. to isomerize the n-butane to produce isobutane;

separating a mixture from the isomerization unit by a de-isobutanizer to produce and form an isomerization unit effluent comprising propane, isobutane, or combinations thereof and an unreacted n-butane stream;

separating a second hydrocarbon mixture comprising propane, n-butane, and isobutane in a second separation unit to produce an overhead stream comprising primarily propane and isobutane, collectively, and a first C4 stream comprising n-butane;

cracking the first C4 stream and/or the unreacted n-butane stream in a first steam cracking unit to produce propylene, ethylene, and benzene;

combining the overhead stream and the isomerization unit effluent to form a combined stream;

separating the combined stream to form a C3 stream comprising primarily propane and a second C4 stream comprising isobutane;

dehydrogenating the isobutane of the second C4 stream in a dehydrogenation unit to produce isobutene in a dehydrogenation unit effluent; and reacting, in an etherification unit, the isobutene of the dehydrogenation unit effluent with an alkanol in the presence of a catalyst to produce an alkyl tert-butyl ether in a product stream.

2. The method of claim 1, further comprising: steam-cracking the C3 stream in a first second steam cracking unit.

3. The method of claim 2, wherein the steam cracking of the second C3 stream is performed at a temperature of 750 to 900° C. and a steam cracker residence time of 0.1 to 0.5 s.

4. The method of claim 1, wherein the isomerization unit comprises an isomerization catalyst comprising $Pt/AlCl_3/Al_2O_3$, $Pt/AlCl_3/zeolite$, $Pt/SO_4^{2-}$—$ZrO_2$, $SO_4^{2-}/ZrO_2$—$Al_2O_3$, or combinations thereof.

5. The method of claim 1, wherein the reaction conditions in the isomerization unit include an isomerization pressure of 20 to 30 bar.

6. The method of claim 1, wherein the isomerization unit effluent comprises 95 to 99.5 wt. % isobutane.

7. The method of claim 1, wherein the dehydrogenation unit effluent comprises 35 to 65 wt. % isobutene.

8. The method of claim 1, wherein the first hydrocarbon mixture and/or the second hydrocarbon mixture comprises liquefied petroleum gas.

9. The method of claim 1, wherein the first hydrocarbon mixture comprises 60 to 80 wt. % n-butane and 20 to 30 wt. % isobutane.

10. The method of claim 1, wherein the etherification unit further produces a recycle stream comprising isobutane.

11. The method of claim 10, further comprising: flowing the recycle stream into the dehydrogenation unit.

12. The method of claim 1, wherein the dehydrogenation unit comprises a dehydrogenation catalyst comprising chromia/alumina, Pt/alumina, or combinations thereof.

13. The method of claim 1, wherein the alkanol comprises methanol, ethanol, or combinations thereof.

14. The method of claim 13, wherein the alkyl tert-butyl ether comprises MTBE, ETBE, or combinations thereof.

15. The method of claim 5, wherein the dehydrogenation unit comprises a dehydrogenation catalyst comprising chromia/alumina, Pt/alumina, or combinations thereof.

16. The method of claim 4, wherein the dehydrogenation unit comprises a dehydrogenation catalyst comprising chromia/alumina, Pt/alumina, or combinations thereof.

17. The method of claim 1, wherein the dehydrogenation unit comprises a dehydrogenation catalyst comprising chromia/alumina, Pt/alumina, or combinations thereof.

* * * * *